United States Patent
Takahashi

(10) Patent No.: US 6,409,968 B1
(45) Date of Patent: Jun. 25, 2002

(54) AUTOMATIC ANALYSIS APPARATUS FOR BIOLOGICAL FLUID SAMPLE AND AUTOMATIC ANALYSIS METHOD THEREFOR

(75) Inventor: Katsuaki Takahashi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/433,718

(22) Filed: Nov. 4, 1999

(30) Foreign Application Priority Data

Nov. 5, 1998 (JP) .......................................... 10-314795

(51) Int. Cl.⁷ .......................... B32B 27/04; G01N 21/00
(52) U.S. Cl. ............................ 422/64; 422/63; 422/67; 422/73; 422/100; 436/807; 436/180
(58) Field of Search ............................ 422/64, 67, 100, 422/63, 73; 436/180, 807, 48

(56) References Cited

U.S. PATENT DOCUMENTS

| | | | |
|---|---|---|---|
| 4,774,055 A | * | 9/1988 | Wakatake et al. |
| 5,501,984 A | * | 3/1996 | Hofstetter et al. |
| 5,698,450 A | * | 12/1997 | Ringrose et al. |
| 5,827,479 A | * | 10/1998 | Yamazaki et al. |
| 5,985,215 A | * | 11/1999 | Sakazume et al. |
| 6,261,521 B1 | * | 7/2001 | Mimura et al. |

FOREIGN PATENT DOCUMENTS

| | | |
|---|---|---|
| JP | 61-270661 | 11/1986 |
| JP | 2-66461 | 3/1990 |
| JP | 2-245665 | 10/1990 |
| JP | 05-005694 | 1/1993 |
| JP | 08-122337 | 5/1996 |

\* cited by examiner

*Primary Examiner*—Ana Fortuna
(74) *Attorney, Agent, or Firm*—Mattingly, Stanger & Malur, P.C.

(57) ABSTRACT

An automatic analysis apparatus comprises a reaction disk having many reaction containers arranged on it. A sample is pipetted from a sample container into the reaction containers, number of which is equal to number of analysis items pre-instructed to be analyzed. At the same time, the identical sample is pipetted into a backup reaction container for backing up the inspection. After that, analysis operation in regard to the instructed analysis items is performed and a first analysis result is obtained. If it is judged from the analysis result that re-analysis is necessary, the backup sample in regard to the sample corresponding to the judgment is pipetted from the backup reaction container into a new reaction container. Then, the analysis operation in regard to the sample is performed again.

4 Claims, 6 Drawing Sheets

AUTOMATIC ANALYSIS APPARATUS FOR BIOLOGICAL FLUID SAMPLE AND AUTOMATIC ANALYSIS METHOD THEREFOR

BACKGROUND OF THE INVENTION

The present invention relates to an automatic analysis apparatus and an automatic analysis method and, more particularly to an automatic analysis apparatus and an automatic analysis method for analyzing analysis items of biological fluid samples such as blood samples, urine samples or the like.

The automatic analysis apparatus for analyzing biological fluid samples is generally constructed So as to analyze various kinds of analysis items, and measures a reaction product produced by reaction between the sample and a reagent in a measuring part. When data of measured result of a sample shows an abnormal value, re-analysis is automatically performed on the identical sample. In order to position a sample container containing a sample at a sample sampling position, there are a method that the sample container is placed on a turntable and the turntable is moved, and a method that the sample container is held in a rack and the rack is moved using a belt conveyer or the like.

Japanese Patent Application Laid-Open No. 2-66461 discloses an automatic analysis apparatus which uses a movable rack for moving sample containers and has a function of re-analyzing samples. In the prior art, a first conveyer lane is disposed between a rack supply portion and a rack standby portion, and two analysis portions each having a reaction disk are disposed along the first conveyer lane, and a sample is pipetted to a reaction container in a reaction disk at a sample sampling position on the first conveyer lane. A second-conveyer lane for re-analysis is arranged in parallel with the first conveyer lane. The standby portion has a reciprocally movable rack transfer table, and receives a rack finished sample sampling from the routine first conveyer lane to hold the rack on the rack transport table until an analysis result of the sampled sample is identified. The rack holding the sample required to be re-analyzed is transferred from the standby portion to the second conveyer lane to be sampled the sample for reanalysis from the rack.

Further, Japanese Patent Application Laid-Open No.2245665 discloses an automatic analysis apparatus which uses a turntable for moving sample containers and is capable of performing re-analysis. The prior art shows an example of an immunity analysis apparatus for inducing an antigen-antibody reaction (immuno-reaction) using a solid carrier. A sample pipetter device having a rotating arm has a pair of disposable tips. At a first analysis, a sample is sucked from a sample container on a sample table into the pair of the disposable tips, and the sample in one of the pair of tips is discharged into a reaction container in a reaction disk to be analyzed. Necessity of a second analysis is judged after the first analysis. If re-analyzing is necessary, the sample contained in the other of the pair of tips is discharged into a reaction container to perform the second analysis.

A ratio of necessity for re-analysis by judgment from a first analysis result to each of analysis items of a sample is approximately 5% of the total. Although most of samples are not necessary to be re-analyzed as described above, it is highly necessary to provide an automatic analysis apparatus with a re-analyzing function. Particularly, in a case of an urgent sample for which an analysis result must be urgently obtained, it is also required to urgently obtain a re-analysis result.

In the case of Japanese Patent Application Laid-Open No.2-66461 described above, the rack holding the plurality of sample containers is made stand by on the rack transport table in the standby portion until first analysis results for all the samples on the rack are obtained. Further, if there is only one sample judged necessary to be re-analyzed among the plurality of samples on the rack, the samples not necessary to be re-analyzed must be transferred on the returning second conveyer lane by being held on the rack together with the sample judged necessary to be re-analyzed. Accordingly, the apparatus requires a complex mechanism unit and an area to keep the rack in standby and to transfer it back.

On the other hand, in the case of Japanese Patent Application Laid-Open No.2-245665, the tips having a special shape are necessary, and the sample pipetter device holding the disposable tip for second analysis is occupied until the first analysis result is obtained. Therefore, the efficiency of processing is extremely decreased because the sample pipetter device can not be used to pipette the other samples during that period.

SUMMARY OF THE INVENTION

An object of the present invention is to provide an automatic analysis apparatus and an automatic analysis method which can perform re-analysis without keeping a sample container after sampling a sample for a first analysis at a standby portion until a result of the first analysis of the sample is obtained.

Another object of the present invention is to provide an automatic analysis apparatus and an automatic analysis method which can perform re-analysis without occupying a sample pipetter device by a sample until a result of a first analysis in regard to the sampled sample is obtained.

A further object of the present invention is to provide an automatic analysis apparatus and an automatic analysis method which can be perform re-analysis without necessity of a special position for keeping a sample container after sampling a sample for a first analysis until a result of the first analysis of the sample is obtained or without necessity of adding a special container.

A still further object of the present invention is to provide an automatic analysis apparatus having a plurality of analysis units which can perform re-analysis of a sample by an analysis unit used first even if a sample container finishing sampling of the sample for the analysis unit used first is transferred to an analysis unit used next before an analysis result of the sample by the analysis unit used first is not obtained yet.

An automatic analysis apparatus which the present invention is applied to comprises a sample transfer device for positioning a sample container containing a sample at a sample sampling position; a reaction disk having a plurality of reaction containers arranged on it; and a pipetter device for pipetting a sample to be analyzed into the reaction container on the reaction disk, and performs operation of analyzing the sampled sample sampled in the reaction container on the reaction disk. The sample container transfer device used may be a rotary type such as a turntable or a type transferring the sample containers on a transfer line by holding them in a rack. There are provided one or more than two analysis units having the reaction disk. In a case where two or more of the analysis units are provided, the sample pipetter devices are respectively provided corresponding to the analysis units.

A concept of the present invention is that an automatic analysis apparatus comprises a control unit for controlling motion of the sample pipetter device so that the sample pipetter device pipettes a backup sample from the sample container at the sample sampling position into one reaction container on the reaction disk when the sample to be analyzed is pipetted, and manages the one reaction container so as to hold the backup sample in the one reaction container until a first analysis result in regard to the sample to be analyzed is obtained, and controls motion of the sample pipetter device to pipette part of the backup sample in the one reaction container into another reaction container based on a judgment that re-analysis to the first analysis result is necessary.

In the automatic analysis apparatus, it is preferable that during operation of analysis in regard to the samples to be analyzed pipetted into the reaction containers, the backup sample in the one reaction container is diluted by mixing with a diluent to obtain a sample diluted in a predetermined ratio (a diluted sample) in order to prepare sample sampling for re-analysis.

Another concept of the present invention is that an automatic analysis apparatus is constructed so that in a case where the sample in the sample container positioned at the sample sampling position to be pipetted is an urgent sample, a backup sample is pipetted from the sample container at the sample sampling position into one reaction container on the reaction disk when the sample to be analyzed is pipetted, and it is judged whether or not a first analysis result in regard to the sampled sample to be analyzed requires to be re-analyzed, and the backup sample is pipetted from the one reaction container into another reaction container on the reaction disk if the re-analysis is required, and then analysis operation of the re-analysis to the sample pipetted in the another reaction container is performed.

In a case where the automatic analysis apparatus comprises a plurality of analysis units, pipetting motion of the backup sample may be stopped when an amount of the sample contained in the sample container before sampling is smaller than a sum of an amount of the sample necessary for the plurality of analysis units and an amount of the backup sample.

A further concept of the present invention is that an automatic analysis apparatus comprising a plurality of analysis units and a sample container transfer mechanism capable of positioning the sample container containing the sample at a sample sampling position provided corresponding to each of the analysis units, wherein the plurality of analysis units include at least an immune item analysis unit and a biochemical item analysis unit; a sample container containing a specific sample requiring analyses by both of the immune item analysis unit and the biochemical item analysis unit being positioned at the sample sampling position for the immune item analysis unit before being positioned at the sample sampling position for the biochemical item analysis unit; at the immune item analysis unit, the corresponding sample pipetter device pipetting a backup sample from the sample container at the sample sampling position into the reaction container on the reaction disk of the immune item analysis unit when the sample to be analyzed is pipetted; the sample for the re-analysis being pipetted from the reaction container containing the backup sample into another reaction container on the reaction disk of the immune item analysis unit when a first analysis result in regard to the sample to be analyzed of the immune item analysis unit requires re-analysis.

DESCRIPTION OF THE PREFERRED EMBODIMENTS

Figure 1:
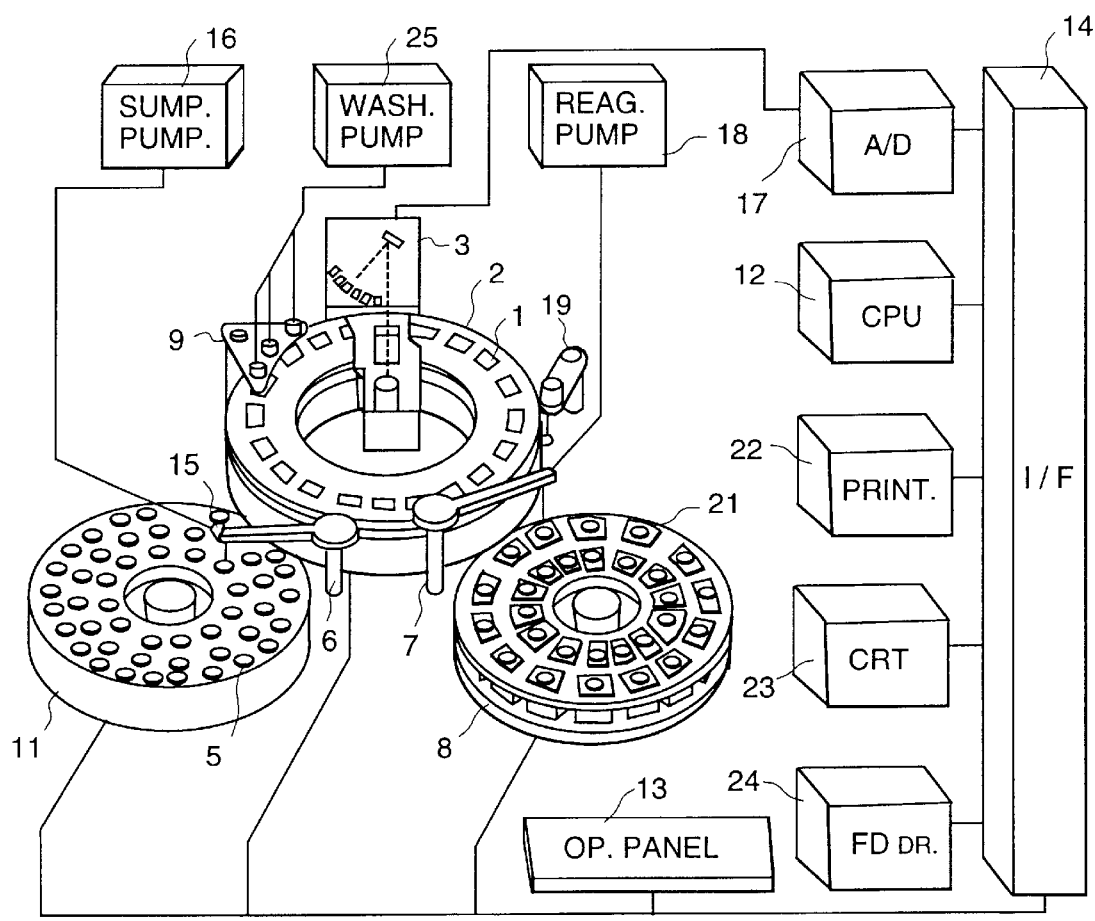
FIG. 1 is a schematic view showing the overall construction of an embodiment of an automatic analysis apparatus in accordance with the present invention.

FIG. 1 shows the overall construction of an embodiment of an automatic analysis apparatus in accordance with the present invention. This embodiment comprises one analysis unit having a reaction disk 2 on which a plurality of transparent reaction containers 1 are arranged. The reaction disk 2 is rotatable both clockwise and counterclockwise.

Referring to FIG. 1, a plurality of sample containers 5 containing samples are arranged on a sample disk 11 and each of the sample containers is positioned at a sample sampling position by rotating motion. After pipetting motion of the samples to all the sample containers, the sample disk 11 is exchanged for a new sample disk on which samples not transacted are set. A computer 12 controls motion of each mechanism in the automatic analysis apparatus through an interface 14. The rotating motion of the sample disk 11 is controlled so that corresponding sample containers 5 are stopped at the sample sampling position while each of the samples is pipetted to the reaction containers number of which is equal to number of instructed analysis items and to a reaction container for backup. A sample pipetting device 6 having a rotatable arm for holding a pipette nozzle 15 performs operation of sucking and discharging the sample using the pipette nozzle corresponding to motion of a sample pump 16 connected to the pipette nozzle 15. Each of the samples is pipetted to the reaction container 1 for each analysis item by the sample pipetter device 6.

The reaction disk 2 is rotated so that each of the reaction containers 1 passes through a sample adding position, a reagent adding position, a mixing position, an optical measuring position and a container washing position. The reaction container 1 receiving a sample from the pipette nozzle 15 at the sample adding position is moved to the reagent adding position to be added with a reagent corresponding to an analysis item using a reagent pipetter device 7. A plurality of reagent bottles 21 prepared for many kinds of analysis items are selectively positioned at a reagent sucking position by a reagent disk 8. Positioning of each of the reagent bottles can be performed by rotating the reagent disk 8 corresponding to an analysis item allocated to a reaction container stopped at the reagent adding position. The pipette nozzle of the reagent pipetter device 7 performs pipetting motion of sucking and discharging a reagent by action of a reagent pump 18.

The reaction container 1 receiving the reagent is moved to the mixing position to mix the mixture of the sample and the reagent using a mixing device 19. A diluent bottle 26 (FIG. 6) containing a diluent is also placed on the reagent disk 8. The reaction container 1 holding the reaction solution of the sample and the reagent is moved so as to move across a light beam at the optical measuring position of a photometer 3. By doing so, an optical property of the reaction solution having a reaction product is detected by the photometer 3, and the detected signal is input to the computer 12 by way of an analogue/digital converter 17 through the interface 14. The computer 12 calculates a concentration of the analysis item based on a calibration curve prepared in advance, and the analysis result is printed out to a printer 22 and/or displayed on a screen of a CRT 23.

The reaction container 1 completed measurement is moved to the washing position to discharge the reaction solution and to be washed with a detergent solution and water at a reaction container washing unit 9 connected to a container washing pump 25, and the cleaned reaction container is moved toward the sample adding position to receive a new sample. A program for operating each of the mechanisms is stored in a floppy disk memory which is read using an FD drive 24. Analysis conditions such as selection of analysis items for each sample, an amount of pipetting a sample for each analysis item, an amount of pipetting each reagent, a dilution ratio and an amount of pipetting a sample for re-analysis and so on can be input and selected from an operation panel 13 in an interactive manner with a screen on the CRT 23.

Operation of automatic re-analysis in the embodiment of FIG. 1 will be described below, referring to FIG. 2 to FIG. 9. The description will be made here by assuming an operation that the reaction disk 2 repeats a cycle of rotating by one turn and one container distance and stopping during normal analysis operation. The photometer 3 optically measures an absorbance of a reaction solution in each of the reaction containers instantaneously when the row of the reaction containers 1 move across the light beam 4.

Figure 2:
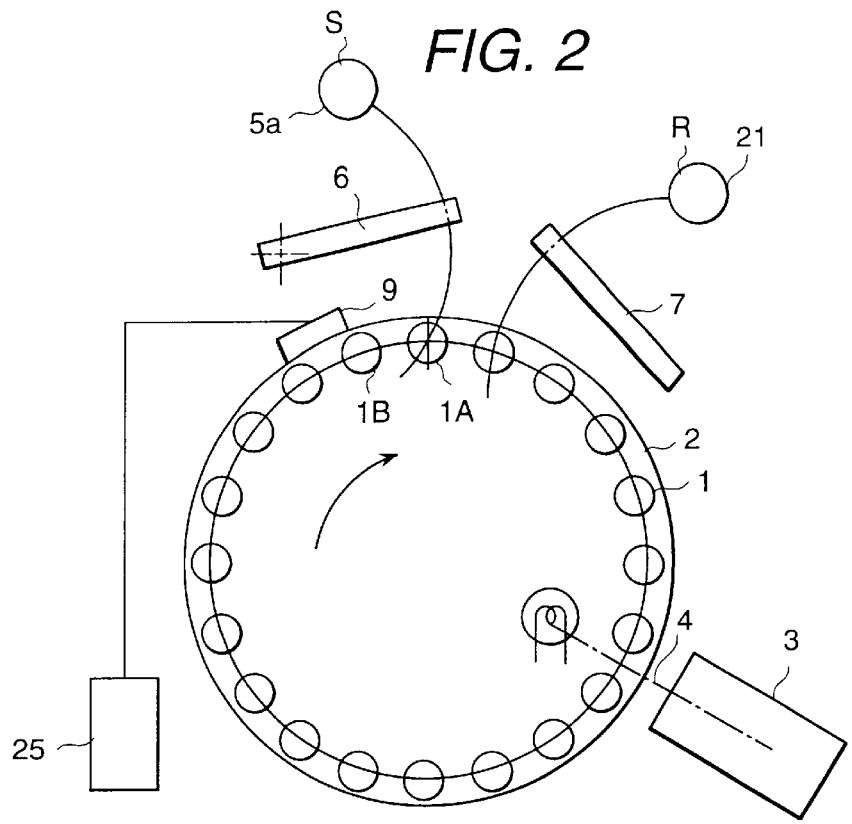
FIG. 2 is a view explaining the pipetting motion of samples in the embodiment of FIG. 1.

Referring to FIG. 2, it is assumed that a sample container 5a containing a sample a pre-instructed to be analyzed in three kinds of analysis items of, for example, α, β and γ is positioned and stopped at the sample sampling position S of the sample disk 11, and that a reagent bottle 21 used for the precedent sample is stopped at the reagent sucking position R of the reagent disk 8. The reaction disk 2 positions and stops a reaction container 1A allocated to analyze the analysis item a at the sample adding position. In this state, the sample pipetter device 6 rotates the pipette nozzle above the sample container 5a and inserts the nozzle tip into the sample inside the sample container 5a to suck and hold the sample a inside the pipette nozzle. Then, the sample pipetter device 6 rotates the pipette nozzle above the reaction container 1A to add the sample a of 2 µl as a sample for first analysis of the analysis item a into the reaction container 1A.

After such pipetting operation, the reaction disk 2 is rotated by one turn and one container distance to position and stop a reaction container 1B at the sample adding position. At the same time, the reagent disk 8 positions the reagent bottle 21a for the analysis item α at the reagent sucking position. The sample disk 11 is not moved, and the sample container 5a is kept stopping. By doing so, the state shown in FIG. 3 is obtained.

Figure 3:
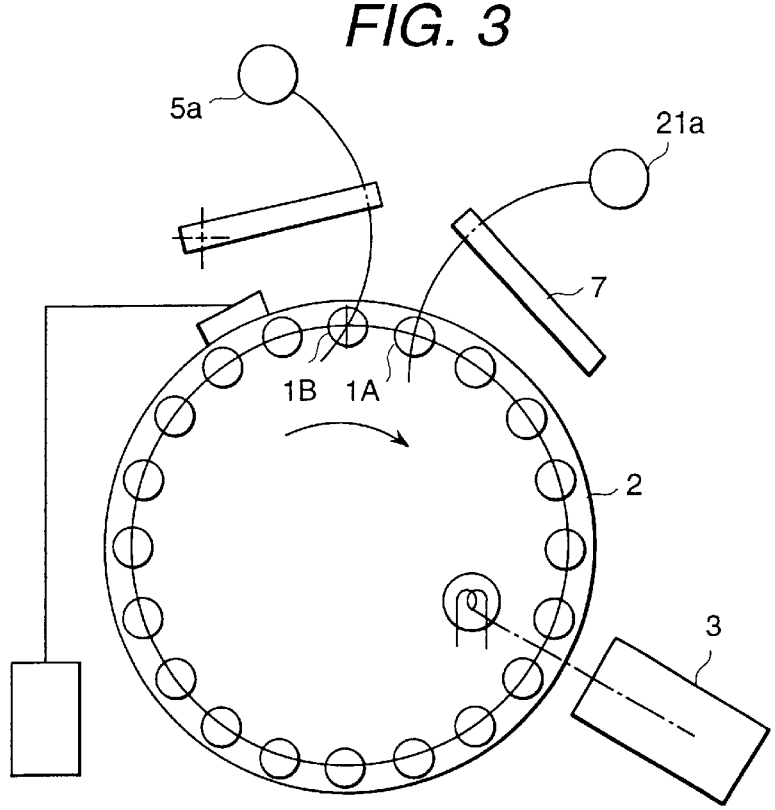
FIG. 3 is a view explaining the pipetting motion of samples at a midway through the process.

Referring to FIG. 3, the sample pipetter device 6 pipettes the sample a for a first analysis of the analysis item β of 3 µl from the sample container 5a into the reaction container 1B. At the same time, the reagent pipetter device 7 pipettes a preset amount of the reagent for the analysis item α from the reagent bottle 21a into the reaction container 1A stopped at the reagent adding position. After that, the reaction disk 2 is rotated by one turn and one container distance to position and stop the reaction container 1C at the sample adding position. At the same time, the reagent disk 8 positions the reagent bottle 21b for the analysis item α at the reagent sucking position. The sample disk 11 is not moved yet, and the sample container 5a is kept stopping. By doing so, the state shown in FIG. 4 is obtained.

Figure 4:
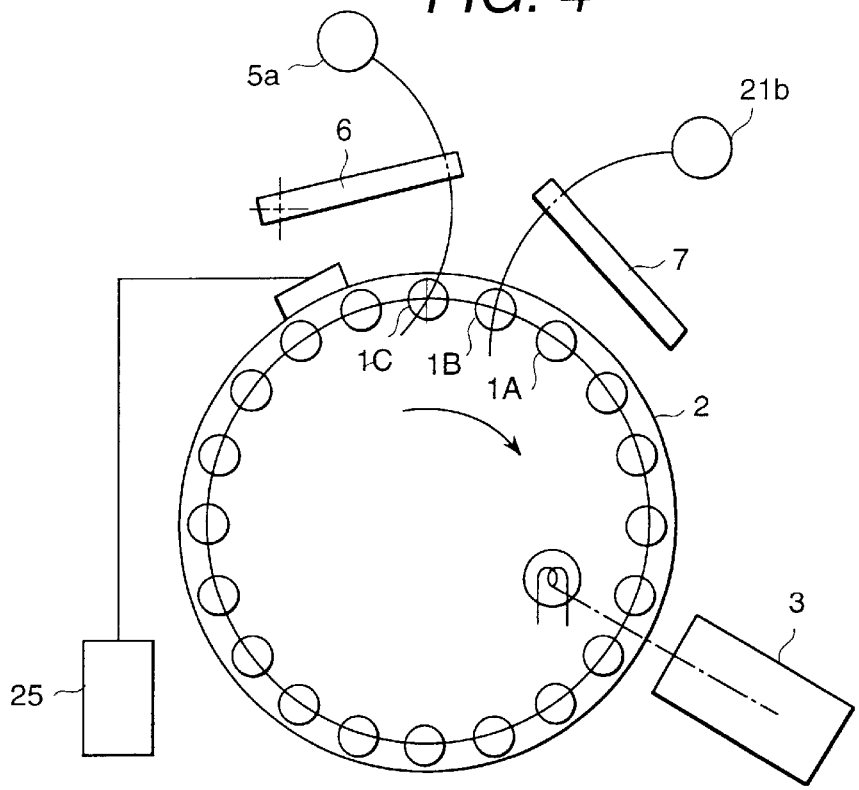
FIG. 4 is a view explaining the pipetting motion of samples.

Referring to FIG. 4, the sample pipetter device 6 pipettes the sample a for a first analysis of the analysis item γ of 4 µl from the sample container 5a into the reaction container 1c. At the same time, the reagent pipetter device 7 pipettes a preset amount of the reagent for the analysis item β from the reagent bottle 21a into the reaction container 1B stopped at the reagent adding position. Successively, the reaction disk 2 is rotated by one turn and one container distance to position and stop the reaction container 1D at the sample adding position. At the same time, the reagent disk 8 positions the reagent bottle 21c for the analysis item γ at the reagent sucking position. The sample disk 11 is not moved yet, and the sample container 5a containing the sample a is kept stopping. By doing so, the state shown in FIG. 5 is obtained.

Figure 5:
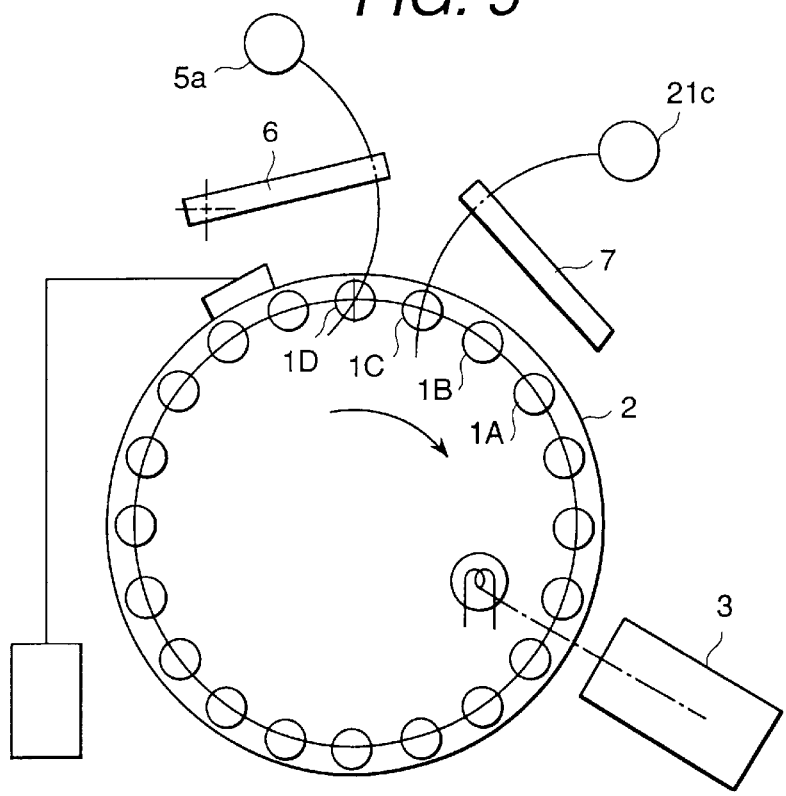
FIG. 5 is a view explaining the pipetting motion of samples.

In FIG. 5, the reaction container 1D on the reaction disk 2 is allocated to receive a backup sample for insuring against a case of necessity of the sample a for re-analysis. That is, in a case of performing first analyses on three items, one or more additional reaction containers are used for receiving the sample a in addition to the three reaction containers for the predetermined analysis items. In other words, the sample pipetter device 6 pipettes the identical sample to reaction containers number of which is larger than number of the instructed analysis items by one or more.

Referring to FIG. 5, the sample pipetter device 6 pipettes the sample a as a backup sample a of 80 µl from the sample container 5a into the reaction container 1D. At the same time, the reagent pipetter device 7 pipettes a preset amount of the reagent for the analysis item γ from the reagent bottle 21a into the reaction container 1C stopped at the reagent adding position. Successively, the reaction disk 2 is rotated by one turn and one container distance to position and stop the reaction container 1E at the sample adding position. At the same time, the reagent disk 8 positions the diluent bottle 26 at the reagent sucking position. Further, at the same time, the sample disk 11 is rotated so that a sample container 5b containing the next sample b is positioned at the sample sampling position. By doing so, the sample to be sampled is changed, and the state shown in FIG. 6 is obtained.

Figure 6:
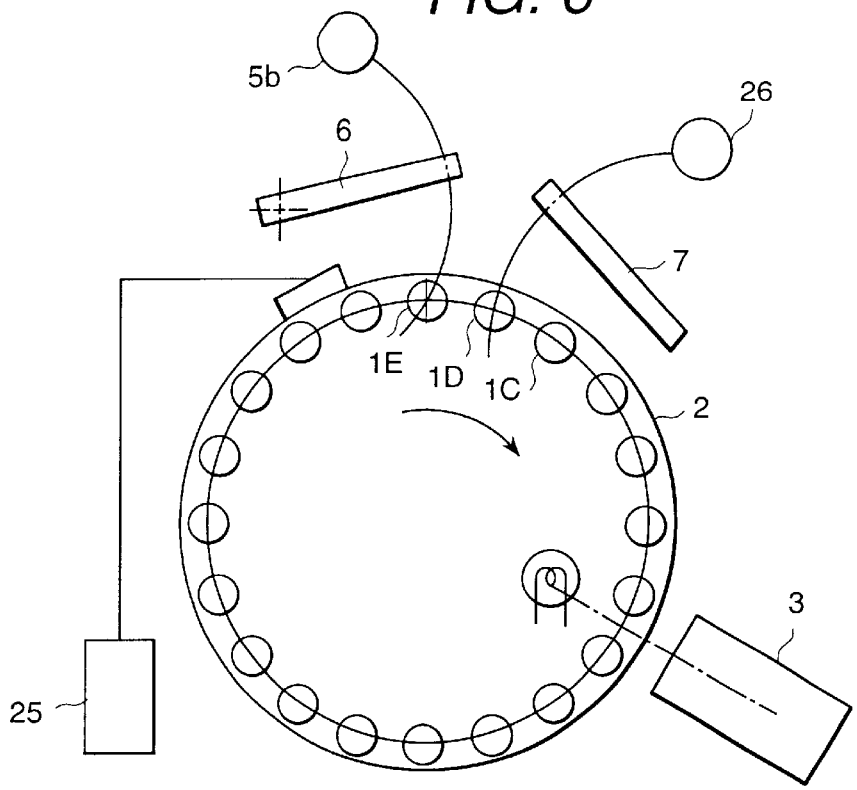
FIG. 6 is a view explaining the diluting motion of a backup sample.

Referring to FIG. 6, the sample pipetter device 6 pipettes the sample b for a first analysis of the analysis item γ of 3 µl from the sample container 5b into the reaction container 1E. At the same time, the reagent pipetter device 7 pipettes the diluent of 160 µl from the diluent bottle 26 into the reaction container 1D stopping at the reagent adding position. Thereby, the sample of 80 µl and the diluent of 160 µl are mixed to dilute the backup sample to three times. When dilution of the backup sample in regard to the sample a is unnecessary, motion of the reagent pipetter device is controlled so as to add the diluent by the computer 12 as a controller.

The sample b is pipetted to the reaction containers for the other analysis items, and at the same time the backup sample is also pipetted to one reaction container. Further, the samples following the sample b are pipetted into the reaction containers on the reaction disk 2 for instructed analysis items and for the backup samples. At 10 minutes after starting the pipetting of the sample a, a first analysis result in regard to each of the analysis items of the sample a can be obtained. At that time, the state of the reaction disk 2 is as shown in FIG. 7.

The controller (computer 12) compares each of the first analysis results for the analysis items $\alpha$, $\beta$ and $\gamma$ with reference values to judge whether or not re-analysis for each of the analysis items is necessary. For example, when a first analysis result shows an abnormally high value or an abnormally low value, it is judged that re-analysis is necessary. It is assumed here that it is judged in regard to the sample a that only the re-analysis for the analysis item $\gamma$ is necessary, and that re-analyses for the analysis items $\alpha$ and $\beta$ are unnecessary.

Figure 7:
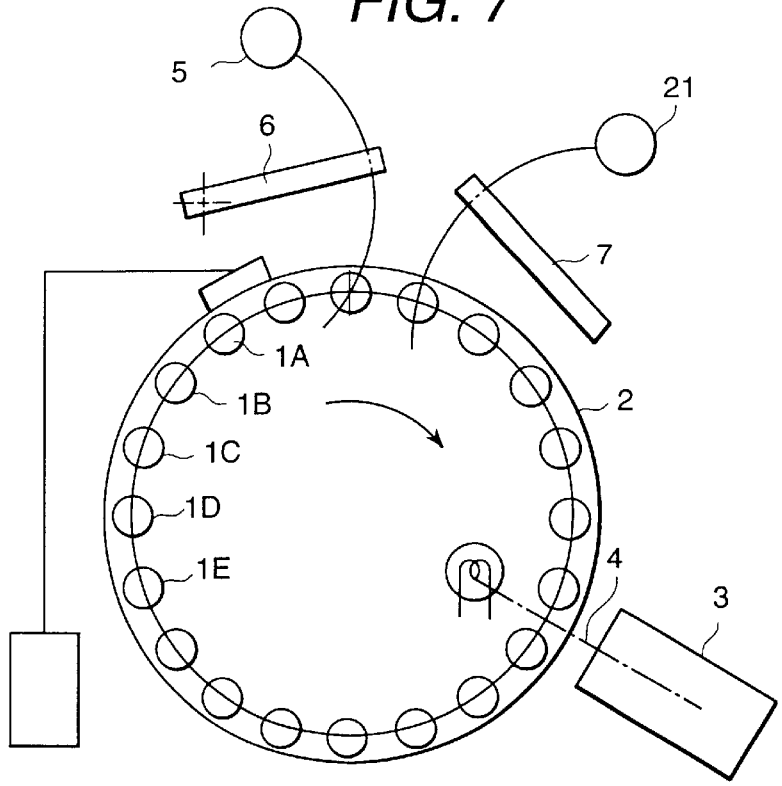
FIG. 7 is a view showing a state of a reaction disk at a time 10 minutes after starting pipetting motion.
Figure 8:
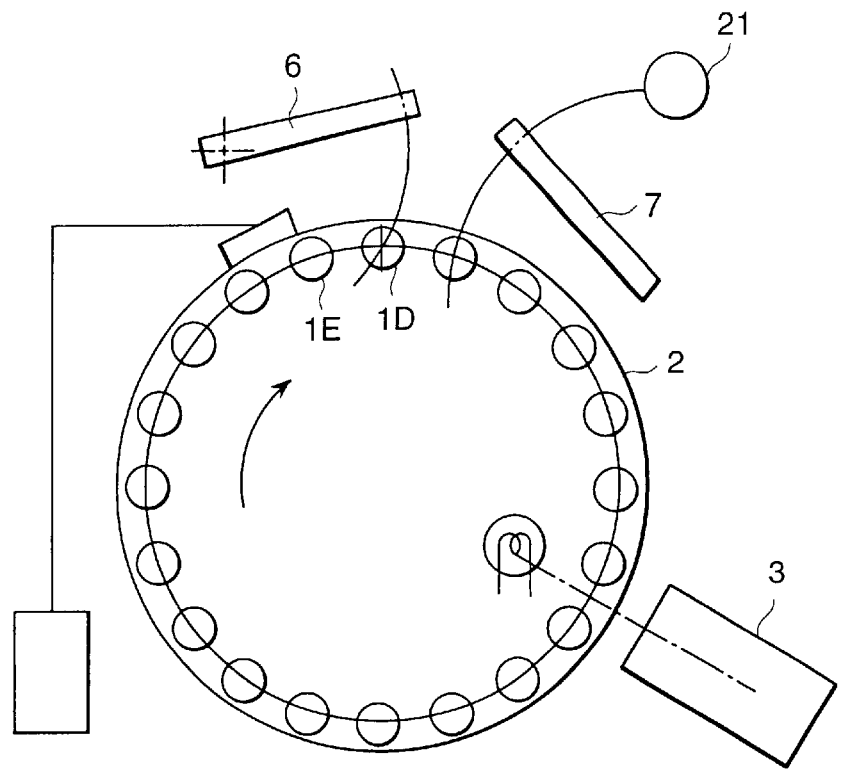
FIG. 8 is a view explaining the pipetting motion of a backup sample.

According to the judgment, the reaction disk 2 is moved from the state of FIG. 7 to the state of FIG. 8. That is, the reaction disk 2 is rotated counterclockwise (in the normal direction) so as to position and stop the reaction container 1D containing the diluted backup sample a of 240 $\mu$l from a halfway position as shown in FIG. 7 to the sample adding position as shown in FIG. 8. After that, the tip of the pipette nozzle 15 of the sample pipetter device 6 is inserted into the diluted sample in the reaction container 1D to suck and hold a preset amount of the sample in the pipette nozzle, and then the pipette nozzle is moved upward. In that state, the reaction disk 2 is rotated counterclockwise (in reverse direction) so as to be recovered to the state of FIG. 7 and stopped. This state is shown in FIG. 9.

Figure 9:
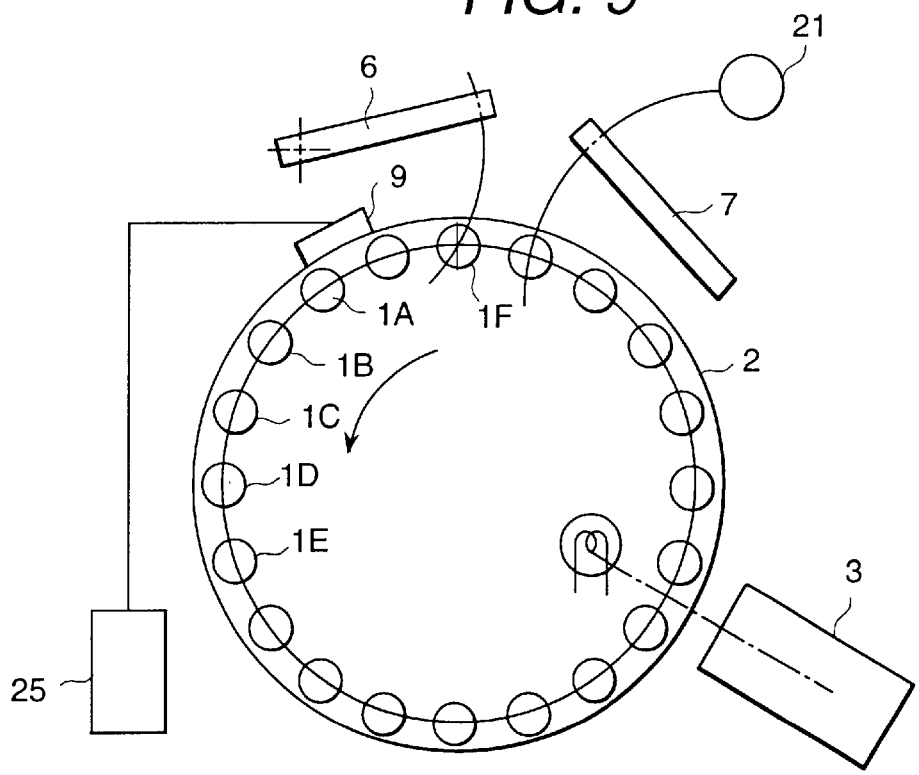
FIG. 9 is a view explaining the pipetting motion of a backup sample.

In the state of FIG. 9, a vacant reaction container 1F is positioned at the sample adding position. The tip of the pipette nozzle 15 of the sample pipetter device 6 is moved downward into the reaction container 1F to discharge the diluted sample held in the pipette nozzle by 4 $\mu$l during stopping of the reaction disk, the reaction container 1A finishing measurement is washed by the reaction container washing unit 9 to be cleaned. After that, the reaction disk 2 is normally moved, and the reaction container 1F containing the sample a for re-analysis is added with the reagent for the analysis item $\gamma$, and mixed, and the reaction solution is optically measured.

In regard to the samples following the sample b, when the first analysis results in regard to the analysis items are obtained, it is judged whether or not the re-analysis is necessary. Part of the backup sample in regard to an analysis item judged necessary to be re-analyzed is pipetted into a new reaction container to perform operation of analysis transaction for the re-analysis. Motion of the sample disk, the reaction disk, the sample pipetter device, the reagent pipetter device and so on is controlled by the computer 12.

It is not necessary that the operation according to the present invention of holding the backup sample for re-analysis in a reaction container is applied to all the samples employ. That is, the automatic analysis apparatus may be constructed so that in regard to most of general samples for routine analyses, the original sample containers are held in the sample disk or a rack, and the original sample positioned container is positioned corresponding to the necessity, similar to the conventional apparatus; and the present invention is applied to an urgent sample. By doing so, in regard to the urgent sample, the backup sample becomes naught if the re-analysis is judged to be unnecessary for any of the analysis items. However, when the re-analysis is judged to be necessary, the result of the re-analysis can be obtained in a very short time, and a ratio of using the reaction containers to the backup sample on the reaction disk can be lowered.

Figure 11:
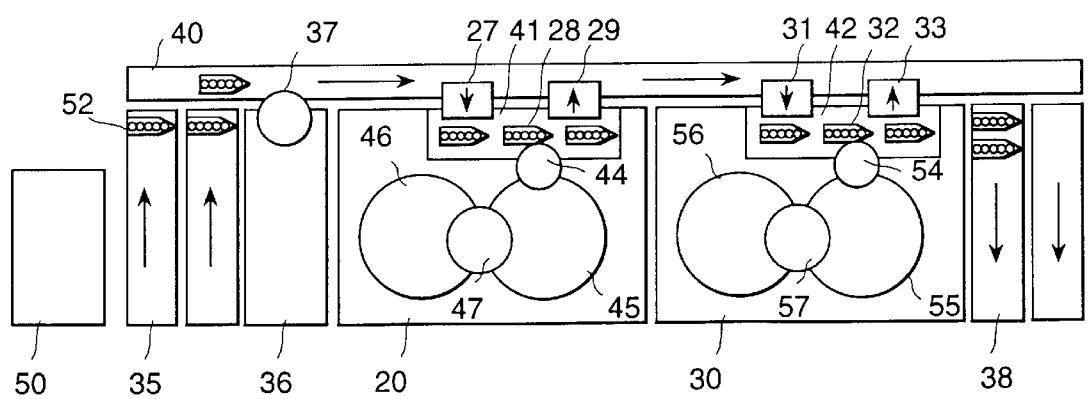
FIG. 11 is a schematic view showing the overall construction of another embodiment in accordance with the present invention.

In that case, the sample container containing the urgent sample is set in an urgent sample area predetermined on the sample disk 11 of FIG. 11 or an urgent sample area provided on a moving path of the pipette nozzle. The computer 12 recognizes request of an urgent sample by detecting setting of the sample container in the area using a container detector or by selecting of an urgent sample measuring instruction button by an operator. Thereby, the sample pipetter device 6 moves the pipette nozzle to a sample sampling position of the urgent sample area to pipette the sample into reaction containers corresponding to the instructed analysis items and to pipette the sample for backup into a reaction container. Operation after that is performed similarly to that described above.

Figure 10:
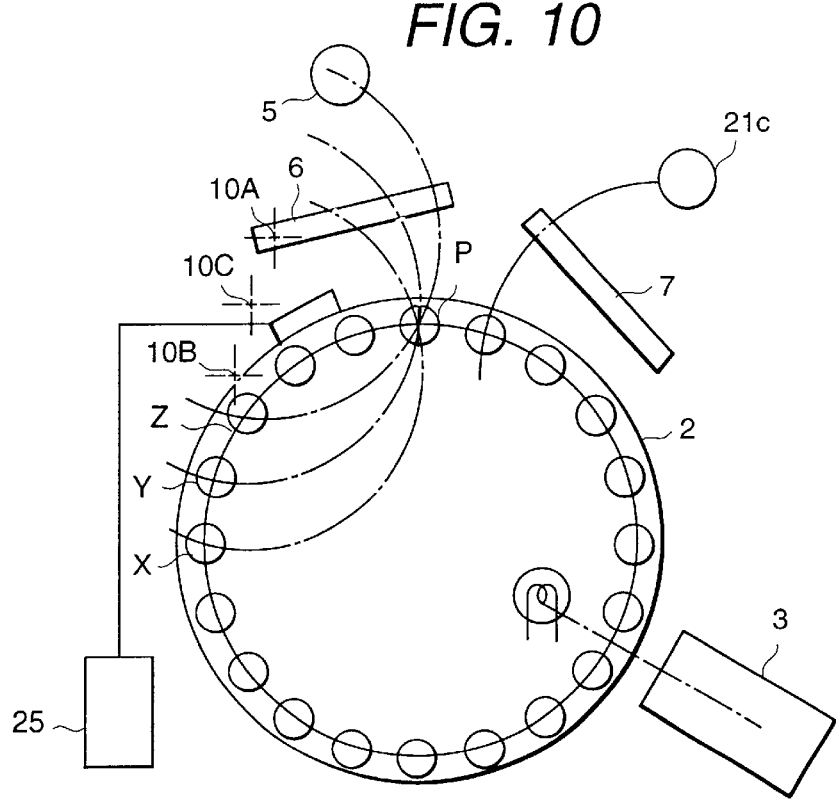
FIG. 10 is a view explaining modifications of the embodiment of FIG. 1.

FIG. 10 is a view explaining three types of modifications of the embodiment of FIG. 1. A first modification is that a motion range of the sample pipetter device is changed instead of rotating the reaction disk in the normal direction and the inverse direction in order to pipette the sample for re-analysis as shown in FIG. 8 and FIG. 9. In this case, the sample pipetter device 6 having the arm rotatable around a rotating center 10A is operated so that samples to be analyzed for a first analysis and a backup sample are pipetted from a sample container 5 into reaction containers positioned at the position P, and so that the backup sample is pipetted from a reaction container containing the backup sample at a position Z into a vacant reaction container at the position P.

A second modification is that two sample pipetter devices are provided. In this case, one of the sample pipetter devices 6 has the arm rotatable around the rotating center 10A to pipette samples to be analyzed for a first analysis and a backup sample into reaction containers positioned at the position P. The other of the sample pipetter devices has an arm rotatable around the rotating center 10B to pipette a backup sample from a reaction container containing the backup sample at a position X into a reaction container at the position P.

A third modification is that one sample pipetter device is constructed so that the rotating center of the arm is horizontally movable. In this case, the reference rotating center of the sample pipetter device 6 is moved so as to be set at the positions 10A, 10B and 10C. For example, a backup sample for the analysis item $\alpha$ is sucked when the reaction container 1D is at the position X and discharged into a new reaction container at the position P, and in the next cycle a backup sample for the analysis item $\beta$ is sucked when the reaction container 1D is at the position Y and discharged into a new reaction container at the position P, and in the further next cycle a backup sample for the analysis item $\gamma$ is sucked when the reaction container 1D is at the position Z and discharged into a new reaction container at the position P. Then, the reaction container 1D is washed. Number of the positions may be several (three positions X, Y, Z in the figure) since the cases required to be re-analyzed occur in not so many items. When the number of the position is short, the reaction container 1D is passed through without being washed, and pipetting may be performed when the reaction container 1D comes to the position X, Y or Z in the second turn at approximately 12 minutes after.

Description will be made below on another embodiment to which the present invention is applied. Analyses on immune analysis items such as CEA, HCG, TSH, T4 extremely avoid being mutually contaminated (carryover) between samples because the analyses deal with infectious diseases. In analyses on biochemical analysis items such as CRE, TP, UA, GOT, a common pipette nozzle is repetitively used by being washed because the carryover between samples is not so severe. On the contrary, in an immune item analysis apparatus, the disposable nozzle tip and the reaction container are replaced by new ones every time when the sample is changed.

FIG. 11 is a schematic view showing the overall construction of an automatic analysis apparatus comprising both of an immune item analysis unit and a biochemical item analysis unit. Although FIG. 11 shows an example comprising two analysis units, three or more analysis units may be disposed. In the analysis units, the identical sample container is positioned at a sample sampling position for each of the analysis units so that a sample may be sampled from the identical sample container.

Referring to FIG. 11, the immune item analysis unit 20 and the biochemical item analysis unit 30 are arranged along a transfer line 40 for transferring a rack from a rack supply unit 35 to rack housing unit 38. The racks 52 holding a plurality of sample containers containing samples are placed side by side in two rack trays of the rack supply unit 35 and transferred pitch by pitch toward the transfer line 40. Each of the racks transferred to the transfer line 40 is once stopped at a position before a sample information reading unit 36, and sample related information attached on each of the sample containers and the rack is read by a bar code reader 37 to be transmitted to a controller 50. On the other hand, the rack housing unit 38 comprises tow rack trays, and receives the rack 52 finishing sample pipetting transaction of at least one of the analysis units from the transfer line 40. Moving and stopping operation of a belt conveyer in the transfer line is controlled by the control unit 50.

A rack holding a sample instructed to be analyzed with immune items is dropped in at a rack receiving area 41 of the immune item analysis unit 20, and the sample is sampled for the desired analysis items at the sample sampling position 28. A rack holding a sample instructed to be analyzed with biochemical items is dropped in at a rack receiving area 42 of the biochemical item analysis unit 30, and the sample is sampled for the desired analysis items at the sample sampling position 32. A rack holding a sample instructed to be analyzed with both immune items and biochemical items is dropped in at the rack receiving areas 41, 42 of the analysis units 20, 30, and the sample is sampled. The rack necessary to be dropped in at both of the immune item analysis unit 20 and the biochemical item analysis unit 30 is preferentially dropped in at the immune item analysis unit 20 first before dropped in at the biochemical item analysis unit 30.

The immune item analysis unit 20 comprises the rack receiving area 41, an exchanger for exchanging a used reaction container to a new one, a reaction disk 45 arranging disposable reaction containers supplied from the exchanger thereon, a sample pipetter device 44 for pipetting from a sample container on a rack at the sample sampling position 28 to a reaction container on the reaction disk 45, a reagent disk 46 mounting reagent bottles corresponding to analysis items, and a reagent pipetter device 47 for pipetting a reagent from the reagent bottle to the reaction container. The sample pipetter device 44 is constructed so that a disposable pipette nozzle tip can be attached to an end of a pipette tube held by a rotatable arm, and that the used pipette nozzle tip can be detached from the pipette tube when pipetting transaction for one sample is finished. The immune item analysis unit 20 comprises a supply unit for supplying many pipette nozzle tips of such a type and a disposing area of the used nozzle tips.

On the other hand, the biochemical item analysis unit 30 comprises the rack receiving area 42, a reaction disk 55 arranging reaction containers repetitively used by being washed, a sample pipetter device 54 for pipetting a sample from a sample container on a rack at the sample sampling position 32 to a reaction container on the reaction disk 55, a reagent disk mounting various kinds of reagent bottles thereon, and a reagent pipetter device 57 for pipetting a reagent from the reagent bottle to the reaction container. A pipette nozzle of the sample pipetter device 54 is repetitively used be being washed. Each of the both analysis units comprises a measuring unit for a reaction solution or a reaction product.

Rack transfer mechanisms 27, 31 operate so as to transfer the rack from the transfer line 40 to the rack receiving areas 41, 42, respectively, and rack transfer mechanisms 29, 33 operate so as to transfer the rack after pipetting transaction from the rack receiving areas to the transfer line 40, respectively.

In the embodiment of FIG. 11, the function of pipetting a backup sample for re-analysis to a reaction container on the reaction disk is provided only to the immune item analysis unit 20, but not to the biochemical item analysis unit 30. The function may be provided to the both analysis units, if necessary. Before performing pipetting transaction of a sample in the biochemical item analysis unit 30, in the immune item analysis unit 20 pipetting for instructed analysis items and pipetting of the backup sample in regard to a sample contained in the corresponding sample container on the rack are performed. Therefore, even if it is judged from the first analysis result of each item in the immune item analysis unit 20 that re-analysis is necessary, it is not necessary that the sample rack once dent out from the rack receiving area 41 is again carried into the rack receiving area 41 through the transfer line 40 to perform pipetting the sample for re-analysis.

Accordingly, the rack finished pipetting transaction in the immune item analysis unit 20 can be immediately transferred to the next biochemical item analysis unit 30, and there is no need to keep the rack standing by at a special area until the first analysis result is obtained. Further, since the rack finished pipetting transaction in the biochemical item analysis unit 30 can be avoided from pipetting transaction of the sample for re-analysis in the immune item analysis unit 20, an effect of carryover between samples can be skillfully excluded.

Pipetting operation of the backup sample in the immune item analysis unit 20 will be not described here in detail in order to avoid repetition because it is similar to that in the case of the above-mentioned embodiment of FIG. 1. To make a long story short, in the immune item analysis unit 20, when the sample pipetter device 44 delivers a sample in a sample container on a rack positioned at the sample sampling position 28 to reaction containers on the reaction disk 45 for the first analysis, the identical sample is delivered to one reaction container on the reaction disk 45 as a backup sample. Then, when the control unit judges based on the result of the first analysis that re-analysis is necessary, the sample for the re-analysis is sampled from the one reaction container containing the backup sample to another reaction container on the reaction disk of the immune item analysis unit.

In the automatic analysis apparatus to which the present invention is applied, in a case where the automatic analysis apparatus comprises a plurality of analysis units each having a reaction disk and a sample pipetter device corresponding to each of the analysis units, when a fluid amount of a sample contained in a sample container before sample sampling is smaller than a total amount of an amount of sample to be analyzed and an amount of a backup sample required in the plurality of analysis units, operation of sampling the backup sample is stopped. By doing so, it is avoidable that the amount of the sample is short due to sampling of the backup sample.

According to the present invention, in regard to a sample having a possibility of re-analysis, a sample container after sampling the sample for a first analysis is not kept at a special standby portion until a result of the first analysis of the sample is obtained, and a sample pipetter device is not occupied by a sample until a result of a first analysis in regard to the sampled sample is obtained. Further, in a case of an automatic analysis apparatus comprising a plurality of analysis units, reanalysis of a sample can be performed by an analysis unit used first even if a sample container finishing sampling of the sample for the analysis unit used first is transferred to an analysis unit used next before an analysis result of the sample by the analysis unit used first is not obtained yet.

What is claimed is:

1. An automatic analysis apparatus comprising a sample transfer device for transferring a sample container so as to pass through a sample sampling position; a reaction disk having a plurality of reaction containers; and a pipetter device for pipetting a sample to be analyzed into the reaction container on said reaction disk, and performing operation of analyzing the sampled sample, which comprises a control unit for controlling motion of said pipetter device so that the sample to be analyzed is pipetted from the sample container stopped at the sample sampling position into the same number of the reaction containers as number of analysis items pre-scheduled to be analyzed and at least one backup reaction container, wherein said control unit controls motion of said pipetter device so as to hold a backup sample in said backup reaction container until a result of a first analysis in regard to the sample to be analyzed is obtained and to pipette part of the backup sample in said backup reaction container into another reaction container for re-analysis.

2. An automatic analysis apparatus according to claim 1, said control unit controls the automatic analysis apparatus so as to dilute the backup sample in said backup reaction container by mixing with a diluent during operation of analysis in regard to the samples to be analyzed pipetted into the reaction containers.

3. An automatic analysis apparatus according to claim 1, which further comprises a plurality of analysis units each having a reaction disk; and a pipetter device corresponding to each of said analysis units, wherein said control unit controls so as to stop sampling motion of the backup sample when an amount of the sample contained in the sample container before sampling is smaller than a sum of an amount of the sample necessary for said plurality of analysis units and an amount of the backup sample.

4. An automatic analysis method in which a sample is pipetted from a sample container at a predetermined position into a reaction container using a sample pipetter device, and the sample is reacted with a reagent to analyze an analysis item, the method comprising the steps of:

pipetting a backup sample from said sample container into another reaction container on said reaction disk when the sample for a first analysis is pipetted from said sample container into said reaction container on said reaction disk;

pipetting the backup sample corresponding to the sample judged necessary to be re-analyzed from a result of the first analysis from said another reaction container into a new reaction container on said reaction disk; and performing operation of re-analysis using the sample in said new reaction container.

\* \* \* \* \*